United States Patent [19]

Clement

[11] Patent Number: 5,300,035
[45] Date of Patent: Apr. 5, 1994

[54] THREADED SCREW TROCAR WITH SEALING MECHANISM

[75] Inventor: Thomas P. Clement, Bloomington, Ind.

[73] Assignee: Mectra Labs, Inc., Bloomfield, Ind.

[21] Appl. No.: 23,578

[22] Filed: Feb. 26, 1993

Related U.S. Application Data

[63] Continuation-in-part of Ser. No. 967,400, Oct. 21, 1992, Pat. No.

[51] Int. Cl.$^5$ ............................................. A61M 5/00
[52] U.S. Cl. ...................................... 604/167; 604/175; 604/256
[58] Field of Search ............... 604/167, 256, 195, 174

[56] References Cited

U.S. PATENT DOCUMENTS

| | | |
|---|---|---|
| 1,657,663 | 1/1928 | Devereux . |
| 4,000,739 | 1/1977 | Stevens . |
| 4,084,718 | 4/1978 | Wadsworth . |
| 4,096,860 | 6/1978 | McLaughlin . |
| 4,134,512 | 1/1979 | Nugent . |
| 4,149,535 | 4/1979 | Volder . |
| 4,164,221 | 8/1979 | Bentley et al. ............. 604/175 |
| 4,240,411 | 12/1980 | Hosono . |
| 4,244,379 | 1/1981 | Smith . |
| 4,311,137 | 1/1982 | Gerard . |
| 4,334,551 | 6/1982 | Pfister . |
| 4,351,328 | 9/1982 | Bodai . |
| 4,422,860 | 12/1983 | Feinstein . |
| 4,424,833 | 1/1984 | Spector et al. . |
| 4,430,081 | 2/1984 | Timmermans ............. 604/256 |
| 4,436,519 | 3/1984 | O'Neill . |
| 4,475,548 | 10/1984 | Muto . |
| 4,491,126 | 1/1985 | Cullor ........................ 604/175 |
| 4,496,348 | 1/1985 | Genese et al. . |
| 4,540,411 | 9/1985 | Bodicky . |
| 4,585,440 | 4/1986 | Tchervenkov et al. . |
| 4,606,347 | 8/1986 | Fogarty et al. . |
| 4,610,665 | 9/1986 | Matsumoto et al. . |
| 4,626,245 | 12/1986 | Weinstein . |
| 4,649,904 | 3/1987 | Krauter et al. . |
| 4,655,752 | 4/1987 | Honkanen et al. ......... 604/256 |
| 4,673,393 | 6/1987 | Suzuki et al. . |
| 4,705,511 | 11/1987 | Kocak . |
| 4,722,725 | 2/1988 | Sawyer et al. . |
| 4,758,225 | 7/1988 | Cox et al. . |
| 4,781,702 | 11/1988 | Herrli . |
| 4,798,594 | 1/1989 | Hillstead . |
| 4,809,679 | 3/1989 | Shimonaka et al. . |
| 4,813,938 | 3/1989 | Raulerson . |
| 4,817,631 | 4/1989 | Schnepp-Pesch et al. . |
| 4,842,591 | 6/1989 | Luther . |
| 4,857,062 | 8/1989 | Russell ........................ 604/167 |
| 4,874,377 | 10/1989 | Newgard et al. . |
| 4,874,378 | 10/1989 | Hillstead . |
| 4,886,507 | 12/1989 | Patton et al. . |
| 4,895,346 | 1/1990 | Steigerwald . |
| 4,895,565 | 1/1990 | Hillstead . |
| 4,909,798 | 3/1990 | Fleischhacker et al. . |
| 4,917,668 | 4/1990 | Haindl . |
| 4,929,235 | 5/1990 | Merry et al. . |
| 4,935,010 | 6/1990 | Cox et al. . |
| 4,950,257 | 8/1990 | Hibbs et al. . |
| 4,960,412 | 10/1990 | Fink . |
| 4,966,588 | 10/1990 | Rayman et al. . |
| 4,978,341 | 12/1990 | Niederhauser . |
| 5,000,745 | 3/1991 | Guest et al. . |
| 5,053,015 | 10/1991 | Gross . |
| 5,059,186 | 10/1991 | Yamamoto et al. . |
| 5,167,636 | 12/1992 | Clement . |

FOREIGN PATENT DOCUMENTS

3042229  5/1982  Fed. Rep. of Germany .

Primary Examiner—Paul J. Hirsch
Attorney, Agent, or Firm—Barnes & Thornburg

[57] ABSTRACT

A sealing mechanism for sealing a trocar used in medical procedures is provided. The cannula is configured to allow passage therethrough of medical devices. The cannula is attached to a conduit piece formed to define at least one channel. A compressible annular seal is positioned in the at least one channel to allow passage through its central aperture of a medical device. An adjustable mechanism is provided for compressing the compressible annular seal to provide an airtight seal across the least one channel. A duckbill flap valve is also positioned in the at least one channel adjacent to the compressible annular seal to receive the medical device after its insertion through the central aperture of the compressible annular seal. Included on the external surface of the cannula is structure for engaging the body wall of a patient for retaining the trocar in place.

21 Claims, 4 Drawing Sheets

THREADED SCREW TROCAR WITH SEALING MECHANISM

BACKGROUND AND SUMMARY OF THE INVENTION

This application is a continuation-in-part of copending application Ser. No. 07/964,400 filed Oct. 21, 1992 pending which is a continuation of application Ser. No. 07/781,985 filed Oct. 24, 1991, now U.S. Pat. No. 5,167,636 to Clement issued Dec. 1, 1992.

This invention relates to trocars used in medical procedures. More particularly, the present invention relates to trocars configured to allow passage of medical devices therethrough while maintaining an airtight seal.

Laparoscopic surgical procedures typically involve pneumatic inflation of a patient's abdominal cavity to increase the accessibility of organs in the abdominal cavity. A trocar is positioned to extend through the abdominal wall of the patient, and secondary cannulas, or other medical devices including graspers, tweezers, or baskets, can be inserted through the cannula to manipulate abdominal organs. To prevent egress through the trocar of air or liquid from the abdominal cavity of the patient, a mechanism for sealing the cannula is required. Such a sealing mechanism must still allow passage through the trocar of medical devices for efficient operation.

Mechanisms for sealing trocars, cannulas, tubes, channels, or the like are known in the art. For example, Patton et al., U.S. Pat. No. 4,886,507, describes a Y-connector for use in angioplasty procedures. The Y-connector has disposed in its main passage a socket that receives a Touhy-Borst O-ring, and a cap with a spigot projecting from it. The cap is threaded onto an outside surface of a socket so that it can be screwed down to bring the spigot into contact with the Touhy-Borst ring to compress it. When the spigot is engaged with the Touhy-Borst ring, flow of blood around external surfaces of the ring, between the O-ring and the socket, is blocked. Axially spaced from, and in alignment with, the Touhy-Borst O-ring, is a membrane having a circular opening to receive and seal a catheter.

Krauter et al., U.S. Pat. No. 4,649,904, discloses a disposable seal having a luer lock and fitting for use with a biopsy channel of an endoscope. A seal is unitarily molded of a soft elastomer to have a double seal arrangement. The seal is formed by an aperture in an end wall and a one-way opening slit through a plate or web behind an end wall.

Hosono, U.S. Pat. No. 4,240,411, discloses a device for sealing an endoscope channel. The sealing device includes a hollow cylindrical member connected at one end to a proximal end of a channel disposed in the sheath of an endoscope, and a tubular member of an elastic material disposed in the hollow cylindrical member. The tubular member is connected at one end sealingly to another end of the hollow cylindrical member. The other end of the tubular member is bent to form a sealing portion that prevents air introduced into a body cavity from flowing back through the channel.

McLaughlin, U.S. Pat. No. 4,096,860, relates to an encatheter adapted for biaxial flow for receipt of a syringe at one end with the main axial passage interconnecting a plastic teflon insertion conduit at the other end and adapted for placement in a blood vessel with a needle. A valve member 38 is received in a cavity 24 defined in a hub 10. The valve member 38 includes a circular or cylindrical wall portion 40 tapering down to a nipple-like element 42 having a slit 44 therethrough. Ordinarily, the slit 44 is in a closed condition to provide for an elastomeric valving in the form of a one-way valve, so that flow can only take place after the valve member 38 has been separated by a tubular member passing therethrough, or by positive pressure.

Muto, U.S. Pat. No. 4,475,548, relates to a fitting for endotracheal apparatus to receive an endoscopic tube. A fitting 25 includes a foam body 31 embraced within a sleeve 30. The foam body 31 is slit end to end, preferably diametrally and preferably not to the edge, by a slit 46. The foam body 31 can be compressed both radially and axially.

Merry et al., U.S. Pat. No. 4,929,235, describes a self-sealing percutaneous tube (e.g., a catheter tube) having a sealing mechanism to prevent blood or fluid leakage. The sealing mechanism includes a space sealing gasket adapted to surround the tube, with a distal sealing element being planar and having a slit. A proximal sealing element is also provided. The proximal sealing element is conical, and has an annular opening at its distal and small end. Optionally, the percutaneous tube includes a side arm flushing member or a female luer lock connection at its proximal end.

O'Neill, U.S. Pat. No. 4,436,519, discloses a hemostasis valve that includes a body having a central passage. A seal having a central aperture therein is mounted in the central passage, along with a diaphragm having a wall member with a slit therein. The diaphragm wall member has an inner bottom diaphragm surface, an outer diaphragm surface, and the slit extends from the inner bottom diaphragm surface to the outer bottom diaphragm surface. Catheters can be forced through the diaphragms' slit and can be withdrawn, allowing the diaphragm slit 1 to close.

Other types of hemostasis valves are known. For example, hemostasis valves are disclosed in U.S. Pat. Nos. 5,000,745; 4,430,081; 4,626,245; and 4,000,739.

Other valves for use in medical instruments, tubing, and/or stoppers or chromatographic injectors are disclosed in, for example, U.S. Pat. Nos. 4,673,393; 4,084,718; 4,515,752; 4,422,860; and 4,013,310.

A trocar for use in endoscopy surgery comprises cannula means for providing a passage into a patient's body for the insertion of a medical instrument. The trocar also includes adjustable sealing means for restricting fluid flow through the cannula when a medical instrument is inserted into the patient's body through the cannula. Housing means attached to the cannula means retains the adjustable sealing means. Adjusting means coupled to the housing means allows manual adjustment of the sealing means to fit different sized medical instruments.

In preferred embodiments, the cannula means includes an externally threaded cannula configured for threaded insertion into a patient's body. The housing means includes a threaded side wall and an internal wall orthogonal to the side wall that cooperate to provide a seat for the sealing means. The internal wall has a central aperture for the passage of a medical instrument.

According to one aspect of the invention, the adjustable sealing means includes a compressible annular seal having a central aperture, and the actuating means includes a threaded cap having an aperture. The cap and side wall are formed to include complementary threads for the threaded engagement of the cap with the side wall. Screwing the cap to the side wall compresses the annular seal between the cap and internal wall to adjust the size of the central aperture of the annular seal to fit around a medical instrument inserted through the apertures in the cap, seal, and internal wall and through the cannula. The compressible annular seal can be a Touhy-Borst type seal.

According to one aspect of the invention, the cannula includes a shoulder attached to the side wall and cooperates with the side wall and internal wall to define an internal chamber in the housing. The sealing means further includes a flap valve positioned in the internal chamber and oriented so as to restrict the egress of fluids from the patient's body through the cannula.

In a preferred embodiment of the invention, the flap valve is a domed duckbill positioned in the internal chamber. The domed duckbill includes a cylindrical side wall extending from a domed center portion. The domed center portion has a slit formed therein to allow the passage of a medical instrument therethrough.

In another preferred embodiment of the invention, the flap valve is a double duckbill. The double duckbill includes a plurality of domed duckbills, each domed duckbill having a domed center portion and a circumferential flange extending therefrom. According to one aspect of the invention, the domed duckbills are positioned in back-to-back relation so that the circumferential flanges abut each other.

Additional objects, features, and advantages of the invention will become apparent to those skilled in the art upon consideration of the following detailed description of a preferred embodiment exemplifying the best mode of carrying out the invention as presently perceived.

BRIEF DESCRIPTION OF THE DRAWINGS

FIG. 7 is a sectional view similar to FIG. 6 showing a double duckbill alternative of the flap valve.

DETAILED DESCRIPTION OF THE DRAWINGS

Figure 1:
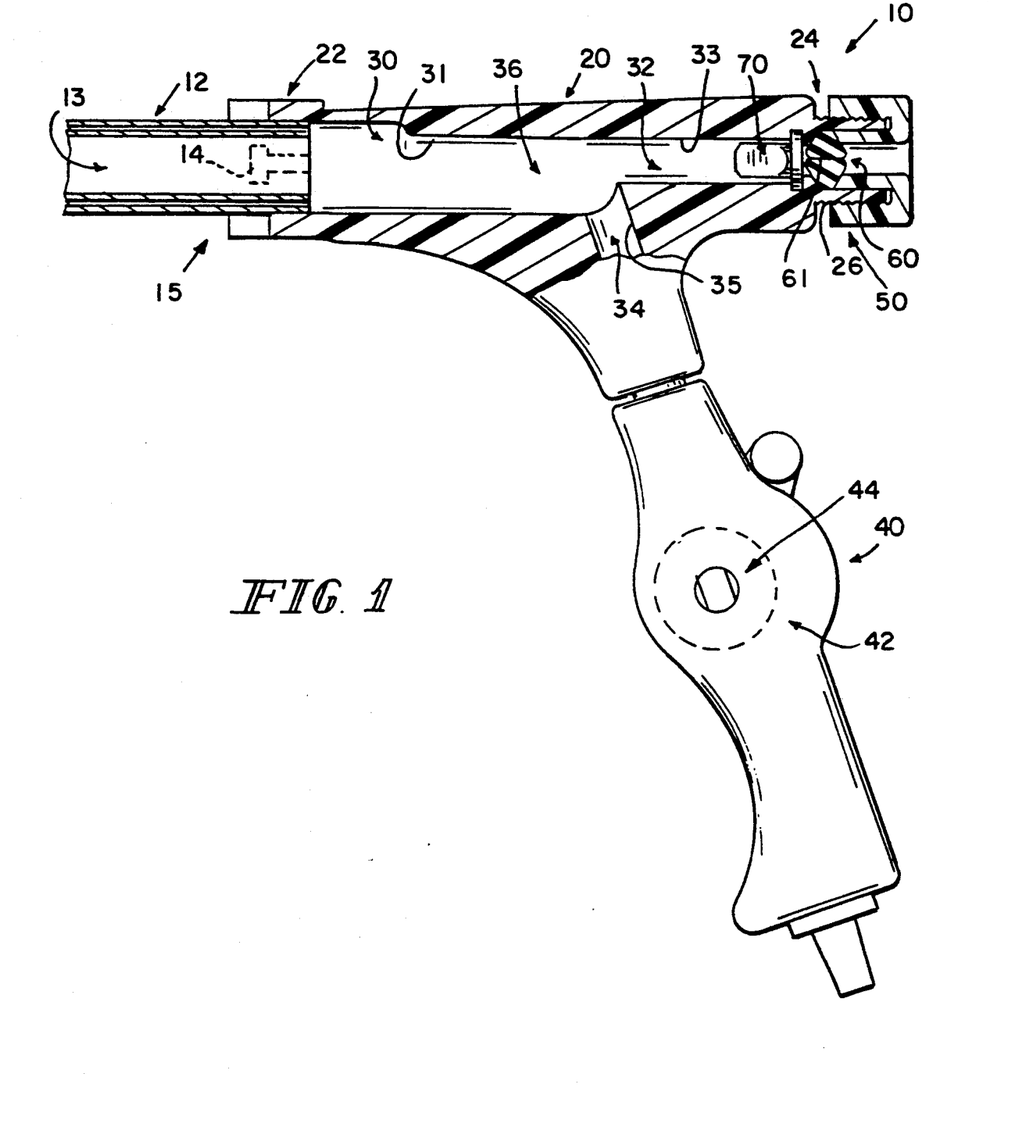
FIG. 1 is a side view of the cannula assembly, partially cut away to illustrate channels defined in an interior of a conduit piece, the channels of the conduit piece connecting to a cannula, to a valve mechanism, and to a sealing assembly that includes a compressible annular seal and a duckbill flap valve.

As illustrated in FIG. 1, a cannula assembly 10 includes a cannula 12 defining a channel 13. The cannula 12 is attached at end 15 to a conduit piece 20 by a lock element 14 configured to engage a matching lock element 22 defined by the conduit piece 20. Luer locks, friction coupling, tab engagement, snap fit attachment, threaded attachment, welded attachment (ultrasonic, RF, or thermal), adhesive attachment, or other conventional attachment methods known to those skilled in the art may be used to attach the cannula 12 to the conduit piece 20. Both removable or permanent attachment mechanisms are contemplated. Optionally, the cannula 12 can be integrally formed with the conduit piece 20.

The illustrated cannula 12 longitudinally extends for at least some portion of its length. Typically, the cannula 12 is substantially straight for it whole length, although curved, partially curved, or angled cannulas may be attached to the conduit piece 20. Typically, the cannula 12 has a tubular configuration, being formed to define a right cylinder having a circular cross section perpendicularly traverse to the longitudinally extending cannula length. However, the cross section can be elliptical, polygonal, or other art recognized cross sectional shapes.

For laparoscopic surgical procedures, a cannula 12 is typically dimensioned to have a length of about 200 millimeters to about 400 millimeters, and a cross-sectional diameter of about 5 millimeters to about 20 millimeters. Preferably, the length of cannula 12 ranges from about 250 millimeters to about 300 millimeters, and its cross-sectional diameter ranges from about 5 millimeters to about 10 millimeters. Dimensions may of course vary for use in non-laparoscopic surgery, being smaller or larger as required.

The cannula 12 is typically constructed from rigid materials such as surgical grade stainless steel or relatively rigid engineering grade plastics such as polycarbonates. If the cannula is short, being less than about 5 centimeters, molded polyethylene or other common thermoplastics can be used to form the cannula, while still maintaining the required rigidity. Optionally, non-rigid, flexible cannulas can be connected to the conduit piece 20. Stiffener elements such as wires can be joined to such flexible cannulas to allow semi-permanent "bends" in the cannula.

The conduit piece 20 is formed to define a first passageway 30 having first passageway walls 31, a second passageway 32 having second passageway walls 33, and a third passageway 34 having third passageway walls 35. The channel 13 of the cannula 12 is directly attached in fluid connection to the first passageway 30. The first, second and third passageways 30, 32, and 34 are dimensioned to permit passage of fluids (including air, water, saline, body fluids) and solids (including body tissue and medical instruments). The passageways 30, 32, and 34 are in common fluid communication, intersecting with each other at a branch 36.

Although metals such as stainless steel can be used to form the conduit piece 20, more commonly the conduit piece 20 is mold-formed as a single integral piece. Rigid thermoset plastics such as polycarbonate or polyethylene are preferred molding plastics. The low cost of molded plastics allows the conduit piece to be disposable, eliminating costly maintenance and sterilization procedures associated with manufacture of non-disposable conduit pieces. Optionally, construction of the conduit piece 20 from optically transparent plastics allows an operator to visually determine if one of the passageways 30, 32, or 34 is completely or partially blocked by solid tissue or other material.

The third passageway 34 of the conduit piece 20 is attached in fluid communication with a valving mechanism 40. The valve mechanism 40 includes a valve body 42 supporting a valve rotor 44 for ease of operation. Preferred valves are described in U.S. Pat. No. 5,019,054, to Clement et al., issued May 28, 1991, the disclosure of which is herein incorporated by reference.

Figure 2:
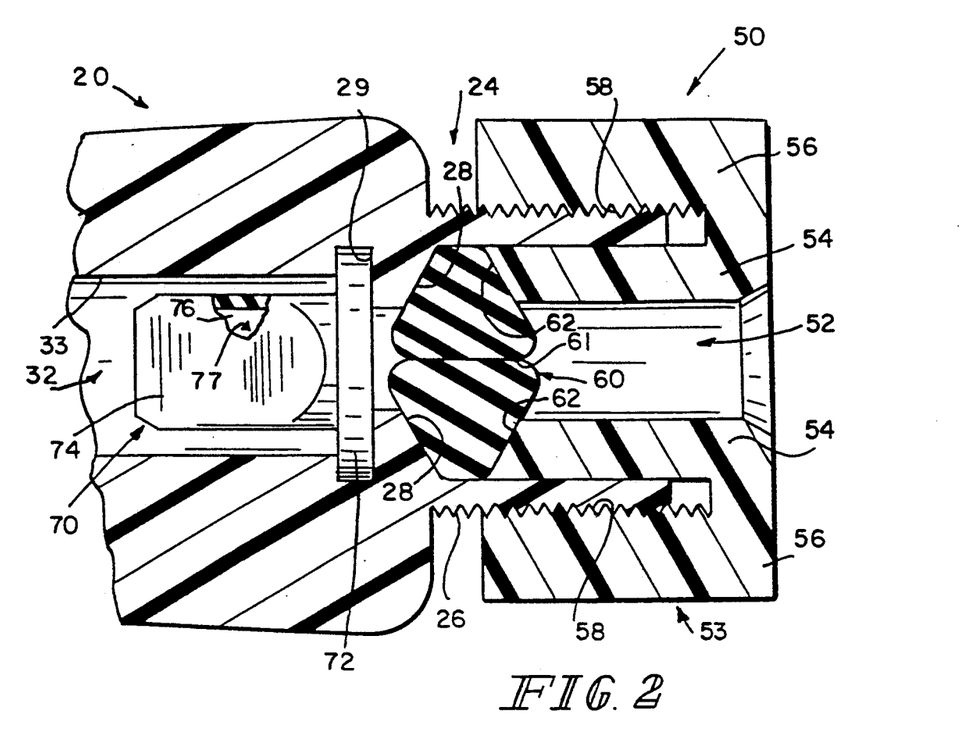
FIG. 2 is a magnified, side cross-sectional view of the sealing assembly illustrated in FIG. 1, showing complete closure of both the duckbill flap valve and the compressible annular seal.

A sealing assembly 50 is attached in fluid communication with the second passageway 32. As best seen in FIG. 2, which is an enlarged view of the sealing assembly 50 indicated in FIG. 1, the sealing assembly 50 includes a movable compression piece 53 having connected inner and outer annular portions 54 and 56, a compressible annular seal 60, and a duckbill flap valve 70. These elements cooperate to form an airtight seal when a medical device 80 (such as the secondary cannula shown in FIG. 3, or other conventional medical devices including graspers, tweezers, baskets, etc.) are inserted therethrough into the passageway 32 and cannula channel 13.

The compressible annular seal 60 is an annular O-ring, normally having a central aperture 61 through which medical devices can be inserted. The seal 60 is constructed of natural or synthetic polymers (e.g., rubber, neoprene, etc.) that are elastically compressible. The seal 60 is illustrated in its fully compressed state in FIG. 2, with the movable compression piece 53 inwardly moved toward the conduit piece 20 to compress the seal 60 therebetween. Optionally, the seal 60 can be coated with friction reducing compounds, including inert, biocompatible silicone oils, fluorinated polymers, or other conventional friction reducers known in the art. Such friction reducing compounds can facilitate inward or outward longitudinal movement of the medical device 80 during its positioning in, or withdrawal from, the channel 13 of the cannula 12.

The compressible annular seal 60 is positioned in a channel 52 defined by an outwardly extending neck 24. The neck 24 is an integrally formed portion of the conduit piece 20, and is formed to present external threads 26 engagable by internal threads 58 defined on the outer annular portion 56 of the movable compression piece 53. The inner annular portion 54 fits into channel 52. Clockwise rotation of the movable compression piece 53 causes a screwing movement of the movable compression piece 53 toward the conduit piece 20, compressing the seal 60 between a first annular wall 28 defined in the conduit piece 20 and a second annular wall 62 defined in the inner annular portion 54 of the movable compression piece 53. Both wall 28 and wall 62 are directed to extend at an oppositely directed (mirror image), non-perpendicular angle relative to the longitudinally extending channels 52, 13, and longitudinally extending passageway 32, to maximize sealing compression.

Those skilled in the art will appreciate that other mechanisms for compressing the compressible annular seal 60 may be employed. For example, instead of screwing mechanisms, those skilled in the art may employ ratchet mechanism, levers, or clamps to move the movable compression piece 53 closer to the conduit piece 20. In addition, perpendicularly directed walls, curved, or multiple angled walls can be used to compress the seal 60.

Situated adjacent to the seal 60, and positioned in the passageway 32, is a duckbill flap valve 70. The duckbill flap valve 70 is integrally formed to have a first flap 74 biasingly directed in sealed engagement with a second flap 76. Both flaps 74 and 76 are integrally joined to a rim 72 having a central aperture 77 through which the medical device 80 can pass. The rim 72 is conformably fitted into an annular notch 29 defined in the second passageway walls 33 of the second passageway 32 to permanently hold the duckbill flap valve 70 in position. The flaps 74 and 76 are separated by a slit (not shown) that allows the flaps 74 and 76 to separate, moving apart as the medical device 80 is inserted therethrough. Like the seal 60, the flaps 74 and 76 can be coated with friction reducing compounds to ease insertion or withdrawal of the medical device 80. As those skilled in the art will appreciate, in addition to the described two-flap duckbill valve, multiple flap valves (including three or more biasingly engaged flaps) can be used in place of the duckbill valve. Alternatively, a single elastic flap positioned to biasingly engage a conduit piece wall or projection is contemplated to be within the scope of the invention.

Figure 3:
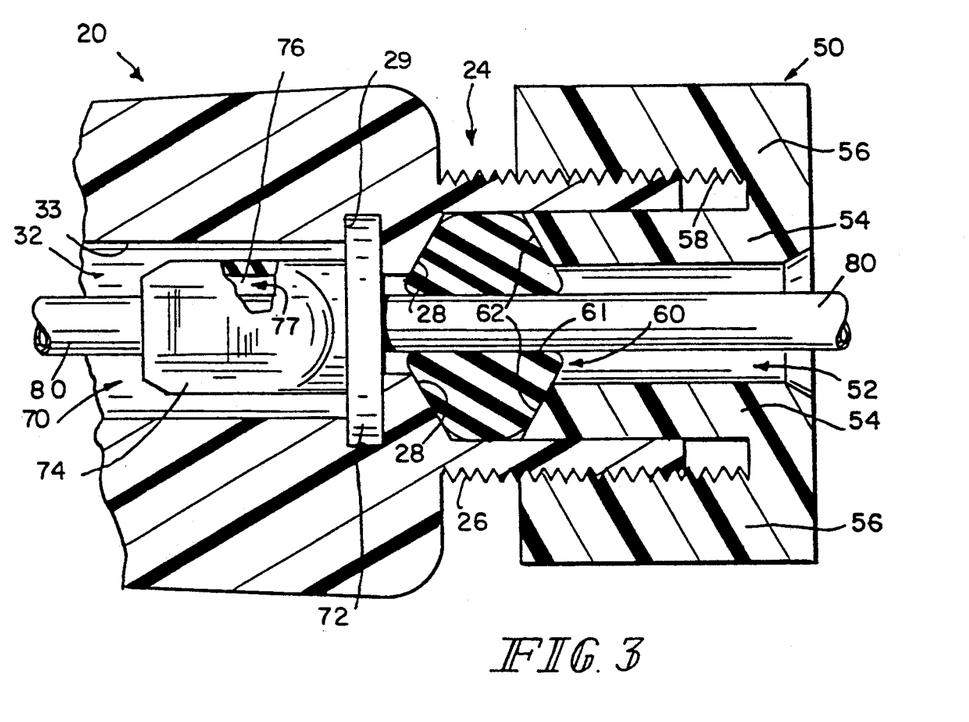
FIG. 3 is a side cross-sectional view of the sealing assembly, shown with a secondary cannula inserted through both the compressible annular seal and the duckbill flap valve to extend onward through the conduit piece and into the channel of the cannula illustrated in FIG. 1.

In operation, as illustrated in FIG. 3, the movable compression piece 53 is unscrewed counterclockwise until seal 60 is in a substantially uncompressed state. The tip (not shown) of the medical device 80 is inserted through the central aperture 61 of the seal 60. The compression piece 53 is then screwed clockwise to compress the seal 60, reducing the size of central aperture 61 and consequently providing an airtight seal against the medical device 80. The movable compression piece 53 is only moved inward far enough to provide an airtight seal by compressing the seal 60, and is not moved inward far enough to lockingly engage the medical device 80 The medical device 80 is then pushed into the conduit piece 20, engaging and parting the flaps 74 and 76 of the duckbill valve. The medical device 80 can then be inserted through the second passageway 32, the first passageway 30, the channel 13 of the conduit 12, and to an operating site.

During withdrawal of the medical device 80, the tip (not shown) is brought back through the duckbill flap valve 70, allowing the flaps 74 and 76 to engage and seal against each other. Sealing engagement of the flaps 74 and 76 is encouraged by a positive pressure in the passageway 32 relative to atmospheric, but the biased construction of the flaps 74 and 76 promotes closure under neutral or even slightly negative pressures. The duckbill flap valve prevents outgassing of air or fluids (or an aerosol mixture of air and fluids) when the medical device 80 is pulled out through the central aperture 61 of the seal 60. After use, the cannula assembly 10 can be disposed of as medical waste.

As those skilled in the art will appreciate, it is not necessary to provide an intermediary channel piece, such as the conduit piece 20, to interconnect the cannula 12 and the sealing assembly 50. Alternatively, it is possible to directly connect the sealing assembly 50 to a conduit appropriately provided with external threads, or other conventional attachment mechanisms.

Figure 4:
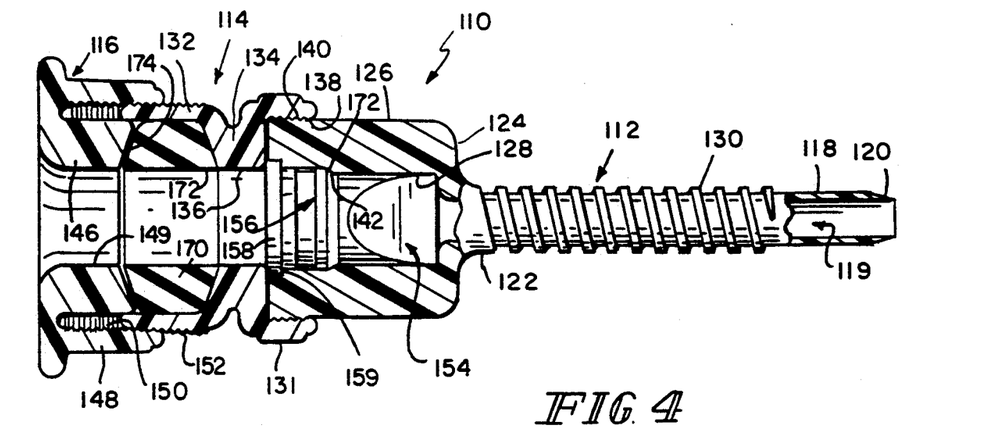
FIG. 4 is a sectional view of a threaded screw type trocar having a compressible annular seal and duckbill flap valve for sealing a central passage of the trocar.
Figure 5:
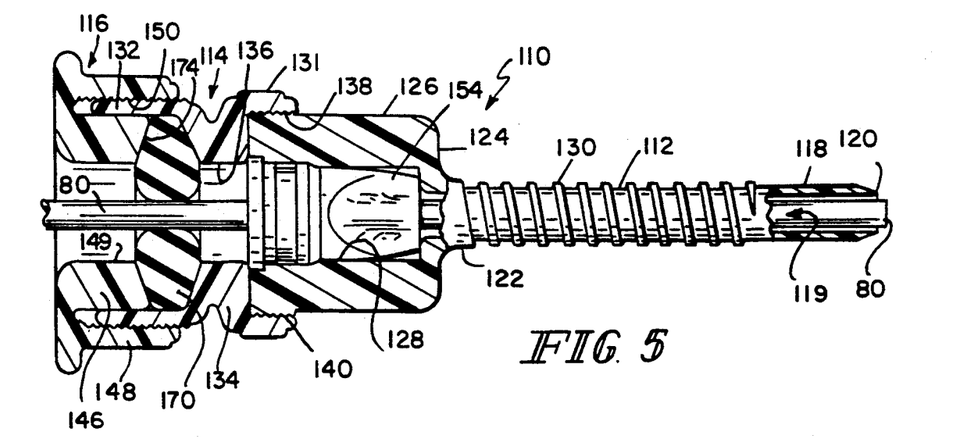
FIG. 5 is a sectional view similar to FIG. 4 showing a medical instrument inserted through the compressible annular seal, the flap valve, and the cannula, with the compressible annular seal closed down to seal the central passage around the medical instrument.
Figure 6:
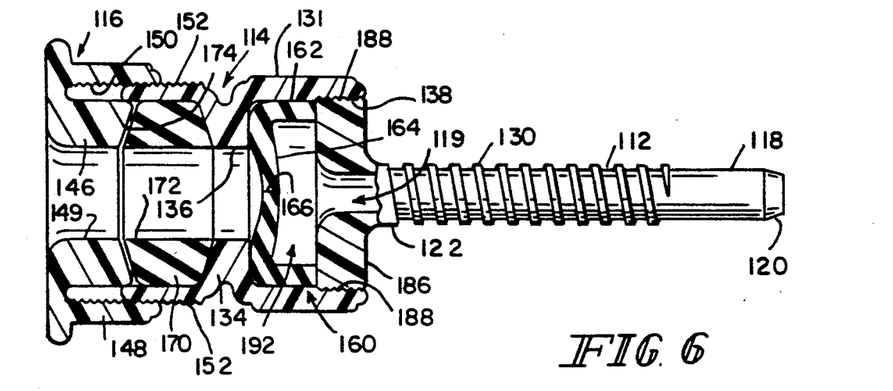
FIG. 6 is a sectional view similar to FIG. 4 showing an alternative embodiment of the flap valve.

A trocar incorporating the compressible annular seal and duckbill flap valve is shown in FIGS. 4-6. The trocar assembly 110 includes a cannula portion 112, an intermediate portion 114, and a compression cap 116. The cannula portion 112 includes a longitudinally extending cannula 118 having an internal channel 119 and a distal end 120 for insertion in a patient's body. The cannula 118 is sized to allow the passage of a medical instrument 80 through the internal channel 119 and into the body of a patient. The proximal end 122 of the cannula 118 is formed to include a shoulder 124 extending radially outwardly from the longitudinal axis of the cannula 118. A cylinder 126 having a central bore 128 is coaxially aligned with the longitudinal axis of the cannula 118 and extends orthogonally from the shoulder 124. External threads 130 extend substantially the length of the cannula 118 from the shoulder 124 to the distal end 120. The threads 130 serve to retain the trocar in the patient's body.

The intermediate portion 114 includes first and second annular side walls 131 and 132. Intermediate the first and second annular side walls 131 and 132, an inwardly extending internal wall 134 is formed to include a central aperture 136 having a diameter at least as large as the internal channel 119 of the cannula 118. Preferably, the first annular side wall 131 is formed to include internal threads 138 for engagement with external threads 140 formed on the cylinder 126.

The compression cap 116 includes connected inner and outer annular portions 146 and 148, respectively. The inner annular portion 146 defines a central aperture 149 coaxially aligned with the aperture 136, the bore 128, and the internal channel 119. The outer annular portion 148 is formed to include internal threads 150 for engaging complimentary external threads 152 formed on the second annular side wall 132. The inner and outer annular portions 146 and 148 are radially separated to allow threaded engagement of the compression cap 116 with the second annular side wall 132, wherein the side wall 132 fits into the gap between the inner and outer annular portions 146 and 148 of the compression cap 116, and the inner annular portion 146 fits inside the second annular side wall 132.

A duckbill flap valve 154 is positioned in the bore 128. The duckbill flap valve 154 is constructed in a fashion substantially similar to the flap valve 70 described with reference to FIGS. 1-3. However, the rim 156 on the duckbill flap valve 154 incorporates a bevelled edge 172 for seating against a shoulder 142 formed in the bore 128. The duckbill flap valve 154 also includes a retaining flange 158. The retaining flange 158 abuts a shoulder 159 formed in the cylinder 126 and lies between the shoulder 159 and the internal wall 134 when the cylinder 126 threadingly engages the first annular side wall 131. Thus, the shoulder 159 and the internal wall 134 cooperate to form an annular slot in which the flange 158 is positioned. The use of the bevelled edge 172 and the shoulder 159 for retaining the flange 158 allows fast and easy assembly while retaining good sealing capability. The formation of an annular slot for the flange 158 maintains the duckbill 154 in position during insertion and withdrawal of a medical instrument through the trocar 110.

FIG. 6 shows an alternative embodiment of the duckbill flap valve 154 of FIGS. 4-5. The cannula 118 is formed to include a shoulder 186 extending radially outwardly from the proximal end 122 of the cannula 118. The shoulder 186 includes external threads 188 that are complementary to the internal threads 138 formed on the first annular side wall 131. A rounded dome duckbill 160 is positioned in an internal cavity 192 defined by the first annular side wall 131 and the internal wall 134 and the shoulder 186. The rounded dome duckbill 160 includes a cylindrical side wall 162 and a domed center portion 164 having a slit 166 formed therein. Ordinarily, the slit 166 is in a closed condition to provide for a one-way valve. Pressure from the abdominal cavity that is transmitted through the internal channel 119 presses against the domed center portion 164, tending to push the edges of the slit 166 into tighter engagement with each other.

As those skilled in the art will appreciate, in addition to the described two-flap duckbill valve and rounded dome duckbill valve, multiple flap valves (including three or more biasingly engaged flaps) may be used in place of the duckbill valve. Alternatively, a single elastic flap positioned to biasingly engage a conduit piece wall or projection is contemplated to be within the scope of the invention.

As shown in FIGS. 4-7, a compressible annular seal 170 having a central aperture 172 is positioned in the intermediate portion 114 to lie against the second annular side wall 132 and the internal wall 134. The inner annular portion 146 of the compression cap 116 cooperates with the second annular side wall 132 and the internal wall 134 to position and retain the compressible annular seal 170 within the intermediate portion 114. The end 174 of the inner annular portion 146 and the internal wall 134 are directed to extend at an oppositely directed (mirror image), non-perpendicular angle relative to the longitudinal axis of the internal channel 119 to maximize sealing compression. Clockwise rotation of the compression cap 116 causes a screwing movement of the compression cap 116 toward the internal wall 134, compressing the compressible annular seal 170 between the inner annular portion 146 and the internal wall 134.

In operation, the compression cap 116 is unscrewed counterclockwise until the compressible annular seal 170 is in a substantially uncompressed state. The tip of a medical device 80 (FIG. 5) is inserted through the central aperture 172 of the seal 170. The compression cap 116 is then screwed clockwise to compress the seal 170, reducing the size of the central aperture 172 and consequently providing an air-tight seal against the medical device 80. The compression cap 116 is only moved inward far enough to provide an air-tight seal by compressing the seal 170, and is not moved inward far enough to lockingly engage the medical device 80. The medical device 80 is then pushed into the bore 128, engaging and parting the flaps of the duckbill valve 154 (or 160). The medical device 80 can then be inserted through the internal channel 119 to the operating site.

During withdrawal of the medical device 80, the tip is brought back through the flap valve 154 (or 160) allowing the valve 154 (or 160) to resiliently return to its original configuration. Sealing engagement of the valve 154 (or 160) is encouraged by the positive pressure in the cannula 118 relative to atmosphere, but the biased construction of the valve 154 (or 160) promotes closure under neutral or slightly negative pressures. The valve 154 (or 160) prevents outgassing of air or fluids (or an aerosol mixture of air and fluids) when the medical device is pulled out through the central aperture 172 of the seal 170.

FIG. 7 shows yet another embodiment of the duckbill flap valve in the form of a double duckbill valve 180. The double duckbill valve 180 includes two domed duckbills 182 and 184. The domed duckbills 182 and 184 are formed to include circumferential flanges 185 surrounding domed center portions 187. The duckbills 182 and 184 are operably positioned in back-to-back relation so that the flanges 185 abut each other and the domed center portions 187 cooperate to define a convex shape, as shown illustratively in FIG. 7. Each domed duckbill 182, 184 also includes a slit 186 formed in the domed center portion 187 to allow the passage of a medical instrument through the double duckbill valve 180.

The trocar 178 is formed to include an interior cavity 188 defined by shoulder 189, cylinder 190, first annular side wall 192, and internal wall 194. An annular shoulder 196 is formed in the first annular side wall 192 so as to extend into the interior cavity 188. The double duckbill 180 is positioned in the interior cavity 188 with the flanges 185 of the domed duckbills 182 and 184 trapped between the cylinder 190 and the shoulder 196 so as to hold the domed duckbills 182 and 184 together in back-to-back relation.

Use of a double duckbill 180 provides several advantages. First, the double duckbill 180 is a two-way valve, whereas conventional duckbill valves are one-way. That is, the double duckbill 180 prevents entry of atmosphere into, as well as escape of fluids from, the body of the patient. A conventional duckbill valve, as illustratively shown in FIGS. 4–6, only restricts fluid from flowing out of the body of a patient. A vacuum formed in the body of a patient will draw fluid (atmosphere) into the body through the conventional duckbill 154 or 160. Second, use of two identical valves in a back-to-back relation simplifies the manufacturing and assembly process and reduces inventory management requirements.

Although the invention has been described with reference to certain preferred embodiments, variations and modifications exist within the scope and spirit of the invention as described and defined in the following claims.

I claim:

1. A trocar for use in endoscopy surgery comprising:
   cannula means for providing a longitudinal passage into a patient's body for the insertion of a medical instrument, said cannula means having an external wall and means for engaging the body wall of a patient to retain the trocar in the patient, said engaging means being disposed on said external wall;
   adjustable sealing means for restricting fluid flow through the cannula when a medical instrument is inserted in the cannula;
   housing means for retaining the adjustable sealing means, said housing means being attached to the cannula means; and
   actuating means coupled to the housing means for manually adjusting the sealing means to fit the medical instrument.

2. The device of claim 1, wherein the engaging means includes external threads formed on the external wall of the cannula means.

3. The device of claim 2, wherein the housing means includes a side wall and an internal wall attached to the side wall, the internal wall having an aperture, the side wall and internal wall cooperating to provide a seat for the sealing means.

4. The device of claim 3, wherein the adjustable sealing means includes a compressible annular seal having a central aperture and the adjusting means includes a threaded cap having a central aperture and the side wall is formed to include complementary threads for threaded engagement of the cap, wherein threaded engagement of the cap and the side wall compresses the annular seal between the cap and internal wall to adjust the size of the central aperture of the annular seal to fit around a medical instrument.

5. The device of claim 4, wherein the compressible annular seal is a Touhy-Borst seal.

6. The device of claim 4, wherein the cannula means includes a cannula attached to a shoulder, the shoulder being attached to the side wall and cooperating with the side wall and internal wall to define an internal chamber in the housing, wherein the sealing means further includes a flap valve positioned in the internal chamber and oriented to restrict the egress of fluids from the patient's body through the cannula.

7. The device of claim 4, wherein the cannula means includes a cannula attached to a shoulder, the shoulder being attached to the side wall and cooperating with the side wall and internal wall to define an internal chamber in the housing, wherein the sealing means further includes a double duckbill valve positioned in the internal chamber and oriented to restrict the flow of fluids into and out of the patient's body through the cannula.

8. The device of claim 1, wherein the adjustable sealing means includes a compressible annular seal having a central aperture, the annular seal being positioned to perimetrally encircle a medical instrument inserted into the longitudinal passage of the cannula.

9. The device of claim 7, wherein the sealing means further includes a flap valve positioned to restrict the egress of fluids from the patient's body through the longitudinal passage of the cannula.

10. The device of claim 7, wherein the sealing means further includes a double duckbill valve positioned to restrict the flow of fluids into and out of the patient's body through the longitudinal passage of the cannula.

11. A trocar for use in passing medical instruments through the abdominal wall of a patient's body in endoscopy surgery comprising:
    a cannula having a longitudinally extending internal passage for guiding such instruments into the patient, a proximal end, a distal end, the distal end being insertable into a patient's body, and means disposed on the cannula for engaging the abdominal wall to retain the trocar in the body of the patient;
    a housing coupled to the proximal end of the cannula and having a central passage coaxially extending from the internal passage of the cannula allowing the insertion of a medical instrument into a patient's body through the central passage and the cannula;
    a compressible annular seal positioned in the central passage; and
    means coupled to the housing for compressing the annular seal to seal the central passage around the medical instrument inserted into the patient's body through the cannula.

12. The device of claim 11, wherein the engaging means includes external threads extending substantially along the length of the cannula.

13. The device of claim 12, further comprising a flap valve positioned to restrict the egress of fluid from the patient's body through the cannula.

14. The device of claim 12, further comprising a double duckbill valve positioned to restrict the flow of fluid into and out of the patient's body through the cannula.

15. The device of claim 11, wherein the housing means includes a side wall, an internal wall orthogonally attached to the side wall, the internal wall having an aperture, the side wall and internal wall cooperating to provide a seat for the compressible annular seal.

16. The device of claim 15, wherein the compressible annular seal has a central aperture and the actuating means includes a threaded cap having an aperture and the side wall is formed to include complementary threads for threaded engagement of the cap, wherein engagement of the cap and the side wall compresses the annular seal between the cap and internal wall to adjust the central aperture of the annular seal to seal the central passage around a medical instrument.

17. The device of claim 16, further comprising a flap valve, wherein the cannula includes a shoulder, the shoulder being coupled to the side wall and cooperating with the side wall and internal wall to define an internal chamber in the housing, the flap valve being positioned in the internal chamber to restrict egress of fluids from the patient's body through the cannula.

18. The device of claim 16, further comprising a double duckbill valve, wherein the cannula includes a shoulder, the shoulder being coupled to the side wall and cooperating with the side wall and internal wall to define an internal chamber in the housing, the double duckbill valve being positioned in the internal chamber to restrict flow of fluids into and out of the patient's body through the cannula.

19. The device of claim 11, further comprising a flap valve wherein the housing includes a side wall and an inwardly extending internal wall orthogonally attached to the side wall, the internal wall having an aperture, and the cannula includes a shoulder coupled to the side wall, the shoulder, side wall, and internal wall defining an internal chamber, and the flap valve is positioned in the internal chamber to restrict the egress of fluids from the patient's body through the cannula.

20. A surgical device for the insertion of a medical instrument into the body of a patient, the device comprising:
an externally threaded cannula having a proximal end, a distal end for insertion into the body of a patient, and an axially extending passage;
a housing coupled to the proximal end of said cannula and having a central passage coaxially aligned with the passage in the cannula for allowing the insertion of a medical instrument into the body of a patient through the central passage and the cannula;
a compressible annular seal having a central aperture, the seal being positioned in the central passage for restricting fluid flow through the central passage and cannula when a medical instrument is inserted through the central passage and cannula;
threaded means for compressing the annular seal to seal the central passage around the medical instrument; and
a flap valve positioned in the central passage for restricting the egress of fluids through the cannula.

21. The device of claim 20, wherein the flap valve includes a double duckbill valve.

* * * * *

UNITED STATES PATENT AND TRADEMARK OFFICE
CERTIFICATE OF CORRECTION

PATENT NO. : 5,300,035
DATED : April 5, 1994
INVENTOR(S) : Thomas P. Clement It is certified that error appears in the above-identified patent and that said Letters Patent is hereby corrected as shown below:

On the title page, item: [63], "Continuation-in-part of Ser. No. 967,400, Oct. 21, 1992, Pat. No." should be -- Continuation-in-part of Ser. No. 964,400, filed October 21, 1992, now U.S. Patent No. 5,282,790.

Signed and Sealed this

Thirtieth Day of August, 1994

*Attest:*

BRUCE LEHMAN

*Attesting Officer*     *Commissioner of Patents and Trademarks*